United States Patent
Stoeber et al.

(10) Patent No.: US 6,406,638 B1
(45) Date of Patent: Jun. 18, 2002

(54) METHOD OF FORMING VERTICAL, HOLLOW NEEDLES WITHIN A SEMICONDUCTOR SUBSTRATE, AND NEEDLES FORMED THEREBY

(75) Inventors: Boris Stoeber, Berkeley; Dorian Liepmann, Lafayette, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/478,913

(22) Filed: Jan. 6, 2000

(51) Int. Cl.[7] .................... H01L 21/302; B44C 1/22
(52) U.S. Cl. ................. 216/11; 216/2; 216/49; 216/79; 438/712; 438/713; 438/719
(58) Field of Search .................. 216/2, 11, 49, 216/79; 438/712, 713, 719

(56) References Cited

U.S. PATENT DOCUMENTS

| | | | |
|---|---|---|---|
| 5,258,107 A | * 11/1993 | Yoshida et al. | 204/129.55 |
| 5,457,041 A | 10/1995 | Ginaven et al. | 435/172.1 |
| 5,676,850 A | 10/1997 | Reed et al. | 216/2 |
| 6,223,591 B1 | * 5/2001 | Nakano | 73/105 |

FOREIGN PATENT DOCUMENTS

| WO | WO 99 64580 | 12/1999 |
|---|---|---|
| WO | WO 00 74764 | 12/2000 |

OTHER PUBLICATIONS

Henry et al., "Microfabricated Microneedles: A Novel Approach to Transdermal Drug Delivery," *Journal of Pharmaceutical Sciences*, U.S., American Pharmaceutical Association, Washington, vol. 87, No. 8, pp 922–925; (May 1998).

McAllister, D.V. et al., "Three–Dimensional Hollow Microneedle and Microtube Arrays," Transducers '99, pp. 1098–1101, Sendai, Japan Dec. 1999.

* cited by examiner

*Primary Examiner*—Randy Gulakowski
*Assistant Examiner*—Shamim Ahmed
(74) *Attorney, Agent, or Firm*—Pennie & Edmonds LLP

(57) ABSTRACT

A method of forming a needle includes the step of anisotropically etching a channel into the back side of a semiconductor substrate. The front side of the semiconductor substrate is then isotropically etched to form a vertical axial surface surrounding the channel. The resultant needle has an elongated body formed of a semiconductor material. The elongated body includes an axial surface positioned between a first end and a second end. The axial surface defines a channel between the first end and the second end. In one embodiment, the first end has a sloping tip with a single circumferential termination point.

40 Claims, 4 Drawing Sheets

METHOD OF FORMING VERTICAL, HOLLOW NEEDLES WITHIN A SEMICONDUCTOR SUBSTRATE, AND NEEDLES FORMED THEREBY

BRIEF DESCRIPTION OF THE INVENTION

This invention relates generally to the fabrication of needles. More particularly, this invention relates to a technique of forming vertical, hollow needles within a semiconductor substrate.

BACKGROUND OF THE INVENTION

Traditionally, needles have been formed with stainless steel. Recently, techniques for forming needles from semiconductors have been disclosed. Several techniques for fabricating needles within a semiconductor substrate have formed the needles in the horizontal plane of the semiconductor substrate. For example, the technique of U.S. Pat. No. 5,928,207, invented by Albert P. Pisano and Kyle S. Lebouitz, and entitled "Microneedle with Isotropically Etched Tip, and Method of Fabricating such a Device", uses isotropic etching to form microneedles in the horizontal plane of a semiconductor substrate. This patent, which is assigned to the assignee of the present application, is incorporated by reference herein.

Another semiconductor fabrication technique for forming needles is disclosed by Neil H. Talbot, Christopher G. Keller, and Albert P. Pisano, in their U.S. patent application Ser. No. 09/044,398, filed Mar. 18, 1998, entitled "Apparatus and Method for Fabricating Needles Via Conformal Deposition in Two-Piece Molds". This technology forms a needle via conformal deposition within a horizontally-oriented chamber defined by a two-piece mold.

Kyle S. Lebouitz and Albert P. Pisano also developed a matrix of isotropically etched tips forming an "abrader" used to abrade epidermis and thereby facilitate transdermal drug delivery. This technology is described in U.S. patent application Ser. No. 09/106,991, filed Jun. 29, 1998, entitled "Transdermal Probe with an Isotropically Etched Tip, and Method of Fabricating such a Device". This patent application, which is assigned to the assignee of the present application, is also incorporated by reference herein. The structure disclosed in the patent application is formed using only isotropic etching. The structure does not have through holes. Further, the structure is not cut into individual needles, as the matrix is used as a single structure forming an abrader.

A related transdermal drug delivery device is disclosed by S. Henry, et al., in "Microfabricated Microneedles: A Novel Approach to Transdermal Drug Delivery," *Journal of Pharmaceutical Sciences*, Vol. 87, No. 8, pp. 922–925, 1998. This publication discloses an array of solid needles that may be used for transdermal drug delivery. An improvement upon this technology is described by several of the same authors in V. D. McAlister, et al., "Three-Dimensional Hollow Microneedle and Microtube Arrays," *Trandsducers* '99 Conference Proceedings, pp. 1098–1101, Sendai, Japan, 1999. The array of needles described in this publication have interior channels. The authors describe how the disclosed arrays can be used for drug delivery or controlled micro-combustion applications.

Despite recent advances in the fabrication of semiconductor-based needles, there still exits a need for improved needle formation techniques. For example, it would be desirable to provide a technique for forming needle walls with various vertical slopes. It would also be desirable to provide a technique for forming needle tips with a variety of shapes.

SUMMARY OF THE INVENTION

A method of forming a needle includes the step of anisotropically etching a channel into the back side of a semiconductor substrate. The front side of the semiconductor substrate is then isotropically etched to form a vertical axial surface surrounding the channel. The resultant needle has an elongated body formed of a semiconductor material. The elongated body includes an axial surface positioned between a first end and a second end. The axial surface defines a channel between the first end and the second end.

The invention provides a variety of techniques for altering the shape of the fabricated needles. For example, a combination of anisotropic and isotropic etching is used to produce needles with steep vertical walls, while isotropic etching alone is used to produce needles with sloping vertical walls that terminate in wide bases. The wide based embodiments operate to withstand relatively large lateral forces. The mask displacement technique of the invention can be used to form a sloping tip with a single circumferential termination point.

BRIEF DESCRIPTION OF THE DRAWINGS

For a better understanding of the invention, reference should be made to the following detailed description taken in conjunction with the accompanying drawings, in which.

Like reference numerals refer to corresponding parts throughout the drawings.

DETAILED DESCRIPTION OF THE INVENTION

Figure 1:
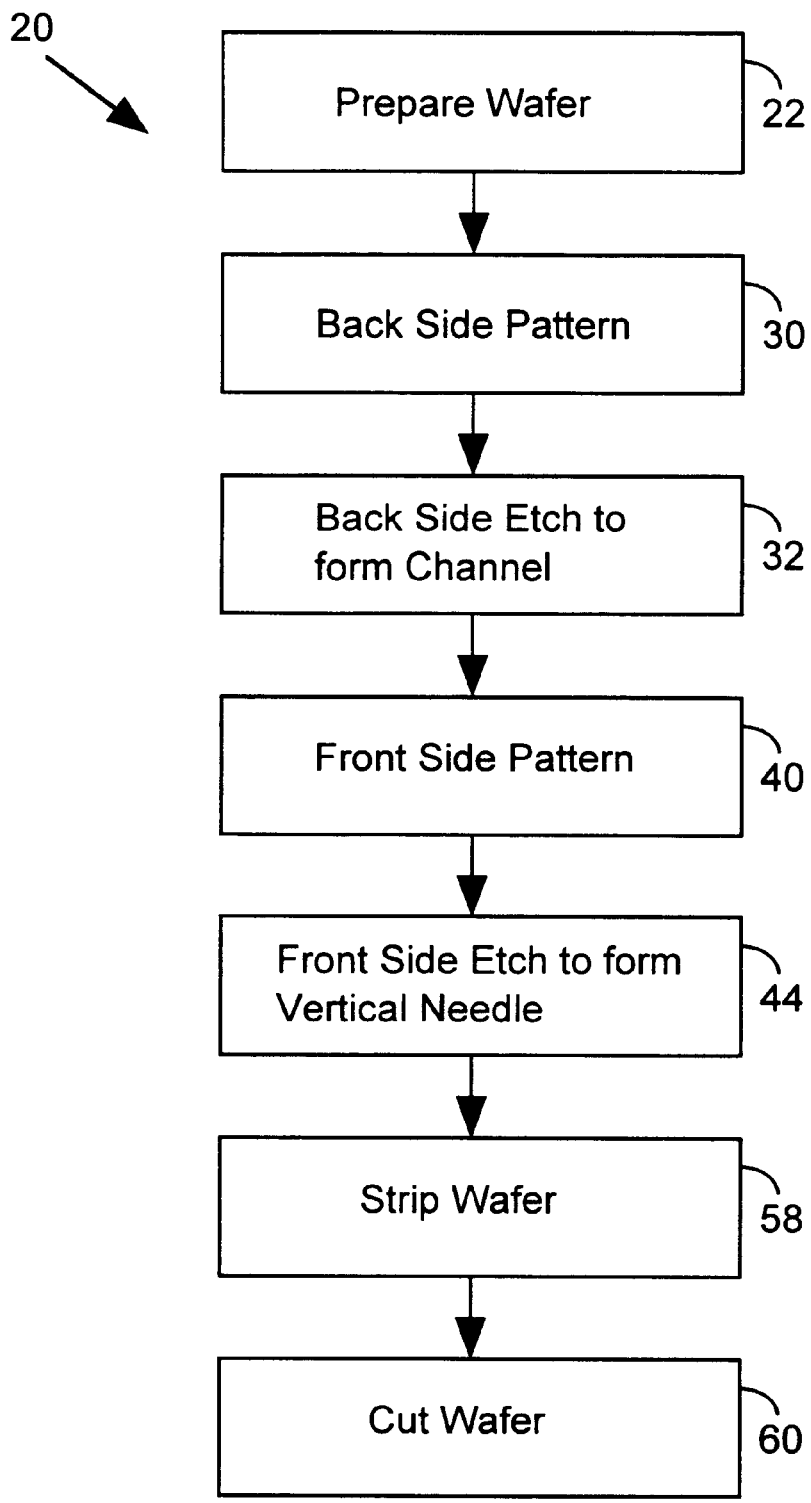
FIG. 1 illustrates processing steps performed in accordance with an embodiment of the invention.
Figure 2A:
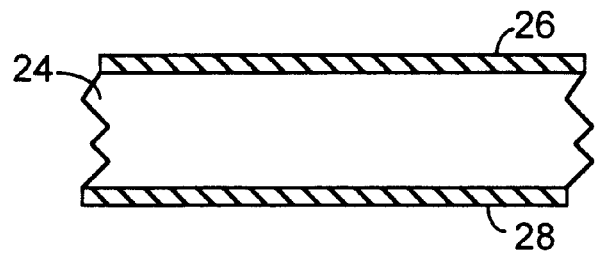
FIGS. 2a–2h provide cross-sectional views of the fabrication of a vertical, hollow needle in accordance with an embodiment of the invention.

FIG. 1 illustrates processing steps 20 performed in accordance with an embodiment of the invention. The first processing step illustrated in FIG. 1 is to prepare a wafer (step 22). By way of example, the starting material may be a <100>silicon wafer that is 500 to 550 $\mu$m thick, and which is polished on both sides. The wafer is cleaned using standard techniques. The wafer is then oxidized, for example, using a horizontal atmospheric pressure reactor at a temperature of 1100° C., to form an approximately 2.0 $\mu$m layer of oxide on the back side and front side of the wafer. FIG. 2a illustrates a wafer 24 with a front side oxide layer 26 and a back side oxide layer 28.

Figure 2B:
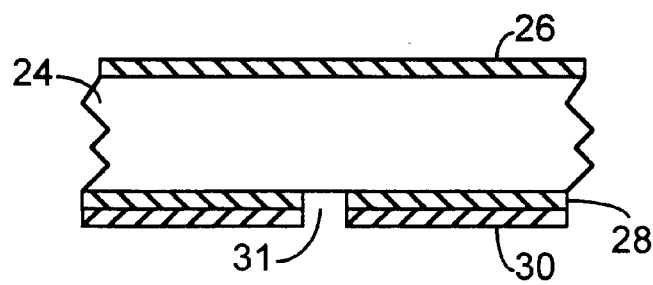

The next processing step shown in FIG. 1 is to pattern the back side of the wafer (step 30). The back side of the wafer is patterned using photolithography in order to define the outline of the back side opening of the channel within the needle. By way of example, the photoresist may be a 1.3 $\mu$m layer of Shilpley S3813 multi-wavelength positive resist, which is exposed, developed, and then hard baked for approximately 30 minutes. The back side oxide layer 28 is then plasma etched, for example, using $CF_4/CHF_3$. This results in the structure of FIG. 2b. FIG. 2b illustrates a back side oxide layer 28 and a photoresist layer 30 with a channel aperture 31 formed therein.

Figure 2C:
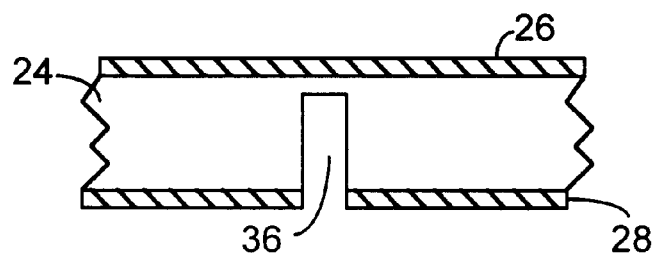

The back side of the semiconductor substrate is then etched to form a channel (step 32). A hole with straight walls is produced using anisotropic Deep Reactive Ion Etching (DRIE). The process is stopped at the front side oxide layer 26 or at some small distance (e.g., 10 $\mu$m) before the oxide layer 26. This results in the structure of FIG. 2c. FIG. 2c illustrates a channel 36 formed within the semiconductor substrate 24. Observe that the channel 36 is formed vertically within the substrate 24.

Figure 3:
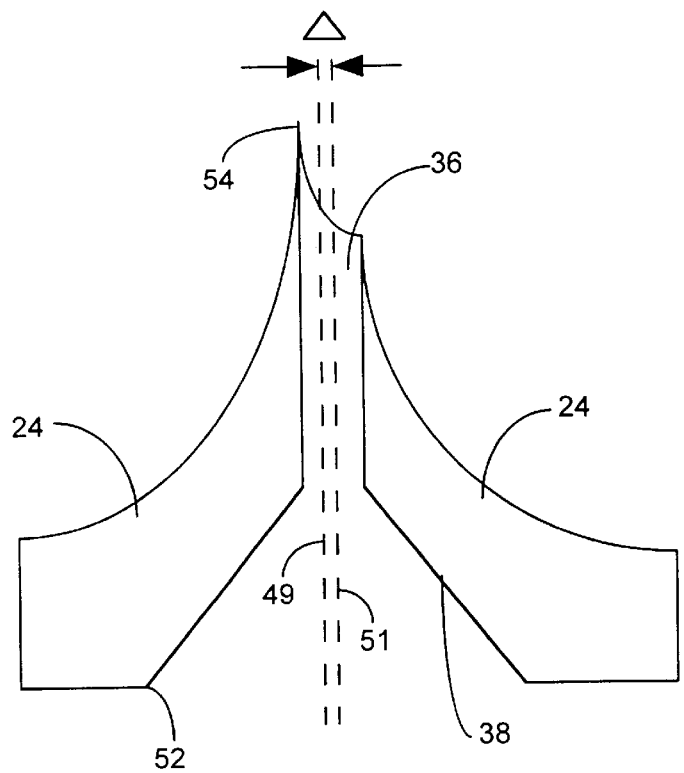
FIG. 3 is an enlarged cross-sectional view of a vertical, hollow needle with a funnel region constructed in accordance with an embodiment of the invention.

In an alternate channel formation operation, a channel with a funnel region is formed. The funnel region is formed by gradually increasing the passivation time relative to the etch time of the DRIE. This results in a reduction in the dimension of the channel as the etch goes deeper into the semiconductor substrate 24. FIG. 3 illustrates a channel 36 with a funnel region 38 formed in accordance with this technique. Those skilled in the art will recognize other techniques for forming the funnel region 38. For example, one can exploit the fact that the etch rate in small holes is much less than the etch rate in wide holes. Therefore, a set of openings with shrinking diameters can be arranged around a channel. An anisotropic DRIE will etch further at the large openings than at the small openings. An isotropic DRIE may then be used to smooth the transitions between stepped etched layers, thereby producing a sloping funnel region.

Figure 2D:
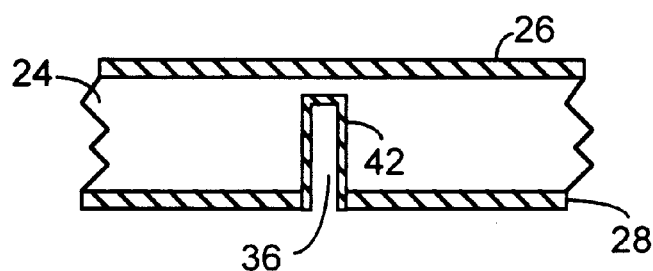

A final operation associated with the back side etch of step 32 is to grow an oxide layer on the wall of the channel to protect the channel during subsequent processing steps. FIG. 2d illustrates a channel oxide layer 42 covering the wall of the channel 36.

Figure 2E:
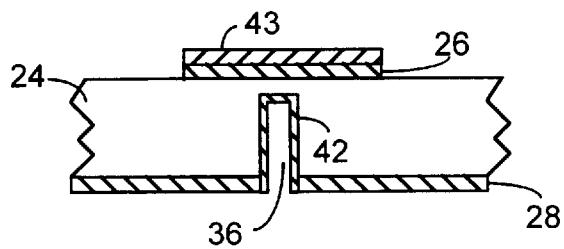

The next processing step illustrated in FIG. 1 is a front side photolithography pattern (step 40). The front side pattern defines the outer perimeter of the needle, as viewed from on top of the needle. By way of example, the photoresist may be a 1.3 $\mu$m layer of Shilpley S3813 multiwavelength positive resist, which is exposed, developed, and then hard baked for approximately 30 minutes. The oxide is then plasma etched, for example, using $CF_4/CHF_3$. This results in the structure of FIG. 2e, which illustrates an etched oxide layer 26 and a front side photoresist layer 43.

The next processing step is to etch the front side of the semiconductor substrate to form a vertical needle (step 44). The needle is created by isotropically under etching the pattern defined by the etched oxide layer 26 and front side photoresist layer 43. An isotropic deep reactive ion etch (DRIE) of the photoresist/oxide mask is performed to a depth of approximately 200 $\mu$m. The isotropic etching forms smooth side walls sloping from a narrow circumference tip to a wide circumference base.

To alter the shape of the needle, the isotropic DRIE may be preceded with an anisotropic etch. In this case, the upper shaft of the needle becomes very steep. In other words, a uniform slope between the base and tip is replaced with a relatively steep transition into the tip. Thus, the isotropic etching step may include an initial anisotropic processing step to form a relatively steep vertical axial surface for the needle.

Figure 2F:
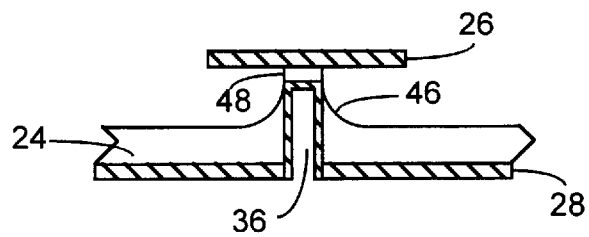
Figure 2G:
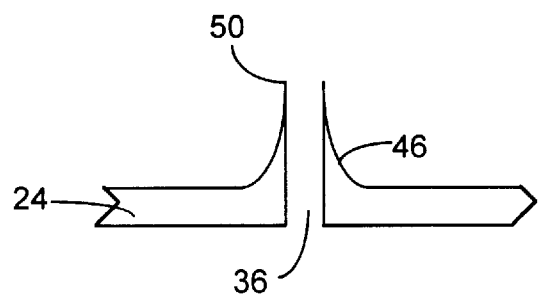

The resultant device at this processing point is illustrated in FIG. 2f. FIG. 2f illustrates isotropically etched sidewalls 46 formed within the substrate 24. The structure of FIG. 2f has a channel end 50 (FIG. 2g) which is uniform around its circumference within a horizontal plane. A tapered channel end may also be formed in accordance with the invention.

More particularly, a sloping tip with a single circumferential termination point may be formed in accordance with the invention. Such a tip is shown in FIG. 3.

This structure may be formed by dislocating the centerline of the channel mask on the back side of the semiconductor substrate from the centerline of the needle mask on the front side of the semiconductor substrate. FIG. 3 illustrates a channel mask center line 51 displaced from a needle mask center line 49 by a distance $\Delta$. This offset produces non-symmetrical etching, which produces a sloping tip with a single circumferential point 54, as shown in FIG. 3.

The next processing step shown in FIG. 1 is to strip the wafer (step 58). This entails removing the oxide, for example, using 5:1 BHF. The wafer is then rinsed and dried, resulting in the structure of FIG. 2g.

Figure 2H:
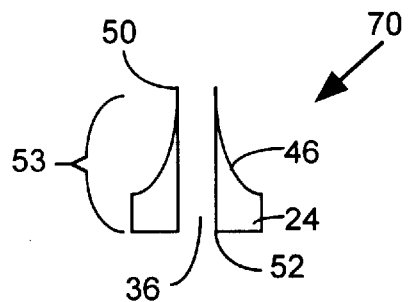
Figure 4:
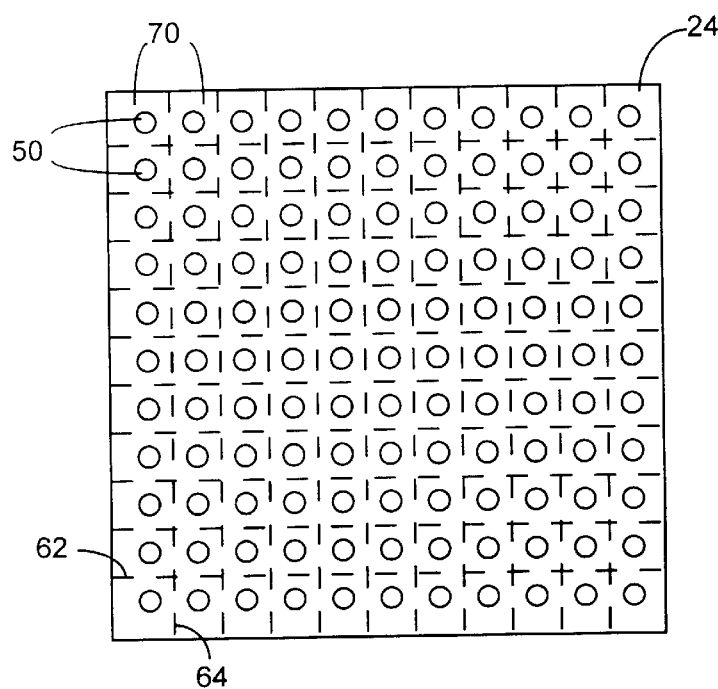
FIG. 4 is a top view of a matrix of vertical, hollow needles formed in a semiconductor substrate in accordance with an embodiment of the invention.

The wafer may then be cut (step 60). FIG. 4 illustrates a top view of a semiconductor substrate 24 including a set of channel apertures 50 associated with a set of fabricated needles 70. The figure also illustrates horizontal scribe lines 62 and vertical scribe lines 64 along which the wafer 24 is cut to form individual needles 70. FIG. 2h illustrates an individual needle 70. The needle 70 includes a channel 36 defined between a front side channel aperture 50 and a back side channel aperture 52. The channel 36 is defined by a vertical axial surface 53 surrounding the channel 36. The vertical axial surface 53 is vertical with respect to the horizontal substrate surfaces that are etched to form the needle 70. Observe that the isotropic etching forms a smoothly sloping side wall 46 between the tip 50 and the relatively wide vertical base.

In many prior art devices the needle is formed in the horizontal surface of a substrate. Thus, for example, a top view of the substrate would show the axial shapes of the needles horizontally formed within the substrate. This configuration limits the number of needles that may be formed within the substrate. In contrast, with the present invention a top view of the substrate, as provided in FIG. 4, shows only the tips 50 of the needles 70, allowing for a relatively dense configuration of needles per substrate.

The exemplary processing disclosed in connection with FIG. 1 results in needles with a vertical height of approximately 200 $\mu$m and a channel diameter of approximately 25 $\mu$m. Naturally, other needle sizes may be implemented in accordance with the invention.

The disclosed needles are advantageously exploited in a variety of biomedical applications. The pointed tips allow them to easily penetrate materials, such as skin. The inner channel of the hollow needles can be used to either inject gases, fluids, suspensions, or to extract gas or liquid that can be analyzed using an integrated device. An array of needles can also be used to pattern a structure with a liquid or with a suspension using specifically spaced channels. Furthermore, the device of the invention can be employed for instrumentation. In addition, it is possible to guide electro magnetic waves through the inner channel. It should also be appreciated that the fabricated structure can be used as a mold for a molding process.

The foregoing description, for purposes of explanation, used specific nomenclature to provide a thorough understanding of the invention. However, it will be apparent to one skilled in the art that the specific details are not required in order to practice the invention. In other instances, well known circuits and devices are shown in block diagram form in order to avoid unnecessary distraction from the underlying invention. Thus, the foregoing descriptions of specific embodiments of the present invention are presented for purposes of illustration and description. They are not intended to be exhaustive or to limit the invention to the precise forms disclosed, obviously many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents.

What is claimed is:

1. A method of forming a needle, said method comprising the steps of:
   anisotropically etching a channel into the back side of a semiconductor substrate; and
   isotropically etching the front side of said semiconductor substrate to form a vertical axial surface surrounding said channel, said vertical axial surface having a rounded cross-sectional profile between a tip of said needle and a base of said needle.

2. The method of claim 1 wherein said anisotropically etching step includes the step of deep reactive ion etching of said backside of said semiconductor substrate.

3. The method of claim 1 wherein said anisotropically etching step includes the step of forming a channel with a funnel region.

4. The method of claim 1 wherein said isotropically etching step includes the step of initially performing an anisotropic etch to alter a profile of said vertical axial surface.

5. The method of claim 1 wherein said isotropically etching step includes the step of deep reactive ion etching of said front side of said semiconductor substrate.

6. The method of claim 1 further comprising the step of depositing a protective material to cover an entire surface of said channel prior to said isotropically etching step.

7. A needle formed by the method of claim 1.

8. A method of forming a matrix of needles, said method comprising the steps of:
   anisotropically etching channels into the back side of a semiconductor substrate; and
   isotropically etching the front side of said semiconductor substrate to form vertical axial surfaces surrounding said channels, said vertical axial surfaces each having a rounded cross-sectional profile between a tip and a base of respective ones of said needles.

9. The method of claim 8 further comprising the step of cutting said semiconductor substrate to produce individual needles.

10. Needles formed by the method of claim 9.

11. The method of claim 8 further comprising step of utilizing said matrix of needles as a mold.

12. The method of claim 8 wherein said anisotropically etching step includes the step of anisotropically deep reactive ion etching.

13. A method of forming a needle, said method comprising the steps of:
   anisotropically etching a channel into the back side of said semiconductor substrate with a channel mask;
   isotropically etching the front side of said semiconductor substrate to form a vertical axial surface surrounding said channel with a needle mask, wherein said channel mask and said needle mask are offset by a predetermined distance such that a plane at which a surface of said channel and said vertical axial surface intersects is unparallel to said front side of said semiconductor substrate.

14. The method of claim 13 wherein said predetermined distance is smaller than a dimension of said channel.

15. The method of claim 13 wherein the vertical axial surface has a rounded cross-sectional profile between a tip of said needle and a base of said needle.

16. The method of claim 13 wherein said anisotropically etching step includes the step of forming a channel with a funnel region.

17. The method of claim 13 wherein said isotropically etching step includes the step of performing an anisotropic etch to alter a profile of said vertical axial surface.

18. The method of claim 13 wherein said isotropically etching step includes the step of deep reactive ion etching of said front side of said semiconductor substrate.

19. The method of claim 13 further comprising the step of depositing a protective material to cover an entirety of said surface of said channel prior to said isotropically etching step.

20. A needle formed by the method of claim 13.

21. A method of forming a needle comprising:
   anisotropically etching a first side of a substrate to form a channel; and
   isotropically etching a second side of the substrate to form a vertical axial surface surrounding the channel, wherein the first side is opposite to the second side.

22. The method of claim 21 wherein said channel is a close-ended channel.

23. The method of claim 22 further comprising etching the second side of the substrate to open the close-ended channel.

24. The method of claim 21 wherein the anisotropically etching step includes deep reactive ion etching of the first side of the substrate.

25. The method of claim 21 wherein the anisotropically etching step includes forming a channel with a funnel region.

26. The method of claim 21 wherein the channel extends from the first side to the second side of the substrate.

27. The method of claim 21 wherein the channel extends from the first side to a predetermined distance short of the second side of the substrate.

28. The method of claim 21 wherein the isotropically etching step includes initially performing an anisotropic etch to produce a steep vertical axial surface.

29. The method of claim 21 wherein the isotropically etching step includes deep reactive ion etching of the second side of the substrate.

30. The method of claim 21 wherein:
   the anisotropically etching step is performed with a first mask having a first center and a first centerline passing through the first center,
   the isotropically etching step is performed with a second mask having a second center and a second centerline passing through said second center, and
   the first centerline is a predetermined distance from the second centerline.

31. The method of claim 22 further comprising depositing oxide to cover an entire surface of the channel prior to the isotropically etching step.

32. A needle formed by the method of claim 26.

33. A method of forming a matrix of needles comprising:
   anisotropically etching a first side of a substrate to form a plurality of channels; and
   isotropically etching a second side of the substrate to form a plurality of vertical axial surfaces, each of the plurality of vertical axial surfaces surrounding one of the plurality of channels, wherein the first side is opposite to the second side.

34. The method of claim 33 wherein at least some of the plurality of channels are close-ended channels.

35. The method of claim 34 further comprising etching the second side of the substrate to open the close-ended channels.

36. The method of claim 33 further comprising cutting the substrate to produce individual needles.

37. Needles formed by the method of claim 36.

38. The method of 33 claim further comprising utilizing the matrix of needles as a mold.

39. The method of claim 33 wherein the anisotropically etching step includes anisotropically deep reactive ion etching.

40. The method of claim 33 wherein the isotropically etching step includes isotropically deep reactive ion etching.

* * * * *